United States Patent
Watanabe et al.

(10) Patent No.: US 10,209,224 B2
(45) Date of Patent: Feb. 19, 2019

(54) PROBE AND OBJECT INFORMATION ACQUISITION APPARATUS USING THE SAME

(71) Applicant: CANON KABUSHIKI KAISHA, Tokyo (JP)

(72) Inventors: Shinichiro Watanabe, Kawasaki (JP); Atsushi Kandori, Ebina (JP); Kazutoshi Torashima, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 272 days.

(21) Appl. No.: 13/795,609

(22) Filed: Mar. 12, 2013

(65) Prior Publication Data
US 2013/0255389 A1    Oct. 3, 2013

(30) Foreign Application Priority Data

Mar. 31, 2012 (JP) .................. 2012-083415

(51) Int. Cl.
*G01D 5/32*    (2006.01)
*G01N 29/00*    (2006.01)
(Continued)

(52) U.S. Cl.
CPC ......... *G01N 29/00* (2013.01); *G01N 21/1702* (2013.01); *G01N 29/2418* (2013.01)

(58) Field of Classification Search
CPC . G01N 29/00; G01N 21/1702; G01N 29/2418
(Continued)

(56) References Cited

U.S. PATENT DOCUMENTS 4,564,877 A * 1/1986 Ezaki .................. G11B 5/00
                                              360/114.01
4,754,544 A * 7/1988 Hanak ............... H01L 31/03921
                                              136/244
(Continued)

FOREIGN PATENT DOCUMENTS

CN    101238754 A    8/2008
CN    102123666 A    7/2011
(Continued)

OTHER PUBLICATIONS

Chinese Office Action issued in counterpart application No. 201310098290.3 dated Jul. 31, 2014, along with its English-language translation—19 pages.
(Continued)

*Primary Examiner* — Son T Le
*Assistant Examiner* — Tarun Sinha
(74) *Attorney, Agent, or Firm* — Venable LLP

(57) ABSTRACT

A probe is provided in which penetration of an acoustic medium into a support layer of an optical reflection member through a pinhole or a scratch on an optical reflection layer is suppressed, occurrence of a solvent crack is suppressed, and noise due to photoacoustic waves that occurs on a receiving surface can be suppressed. The probe includes an element having at least one cell in which a vibration film containing one electrode out of two electrodes that are provided so as to interpose a space therebetween is vibratably supported. The probe further includes a support layer disposed on the vibration film, and an optical reflection layer disposed on the support layer. A protection layer against an acoustic medium is formed on the optical reflection layer.

31 Claims, 3 Drawing Sheets

(51) Int. Cl.
*G01N 29/24* (2006.01)
*G01N 21/17* (2006.01)

(58) Field of Classification Search
USPC .......................................................... 73/655
See application file for complete search history.

(56) References Cited

U.S. PATENT DOCUMENTS

| | | | | |
|---|---|---|---|---|
| 5,156,941 | A * | 10/1992 | Fujita | G06K 19/06046 427/162 |
| 8,144,327 | B2 | 3/2012 | Nakajima et al. | |
| 8,300,224 | B2 | 10/2012 | Nakajima et al. | |
| 2002/0121966 | A1* | 9/2002 | Woodard | G08B 3/10 340/384.6 |
| 2007/0092662 | A1* | 4/2007 | Matsuno | G02B 1/105 428/1.3 |
| 2007/0154788 | A1* | 7/2007 | Hong | H01M 4/13 429/130 |
| 2009/0062655 | A1* | 3/2009 | Saito | A61B 8/4444 600/459 |
| 2009/0264768 | A1* | 10/2009 | Courtney | A61B 5/0062 600/463 |
| 2010/0038993 | A1* | 2/2010 | Umeda | H03H 9/14538 310/313 B |
| 2010/0053618 | A1 | 3/2010 | Nakajima et al. | |
| 2010/0290191 | A1* | 11/2010 | Lin | H01L 23/49816 361/704 |
| 2011/0108838 | A1* | 5/2011 | Kageyama | B06B 1/0292 257/49 |
| 2011/0137166 | A1 | 6/2011 | Klee et al. | |
| 2012/0020188 | A1* | 1/2012 | Mielenz | G01S 7/52004 367/99 |
| 2012/0133941 | A1 | 5/2012 | Nakajima et al. | |
| 2012/0262770 | A1* | 10/2012 | Torashima | G01N 29/2418 359/199.2 |
| 2013/0081471 | A1 | 4/2013 | Akiyama et al. | |
| 2013/0134834 | A1* | 5/2013 | Yoshikawa | B06B 1/0622 310/341 |

FOREIGN PATENT DOCUMENTS

| | | | |
|---|---|---|---|
| JP | 2005198261 A * | 7/2005 | |
| JP | 2006-208050 | 8/2006 | |
| JP | 2009-272824 | 11/2009 | |
| JP | 2009272824 A * | 11/2009 | |
| JP | 2009272824 A1 * | 11/2009 | |
| JP | 2010-075681 | 4/2010 | |
| JP | WO 2011155163 A1 * | 12/2011 | B06B 1/067 |
| WO | 2011/155163 A1 | 12/2011 | |
| WO | WO 2011155163 A1 * | 12/2011 | |

OTHER PUBLICATIONS

Extended European Search Report dated Dec. 22, 2017, in counterpart application EP 13001484.8 (8 pages).

* cited by examiner

PROBE AND OBJECT INFORMATION ACQUISITION APPARATUS USING THE SAME

BACKGROUND OF THE INVENTION

Field of the Invention

The present invention relates to a probe that is used as a photoacoustic probe for receiving photoacoustic waves caused by an object owing to light with which the object is irradiated and includes a capacitive electromechanical transducer, and an object information acquisition apparatus using the same.

Description of the Related Art

Conventionally, ultrasonic probes employing transducers made of piezoelectric material (i.e., electromechanical transducers) have been used. In recent years, capacitive micromachined ultrasonic transducers (CMUT) manufactured using a semiconductor process has been attracting attention. For instance, the capacitive micromachined ultrasonic transducer has cells each including two parallel plane electrodes and a cavity, and can send and receive acoustic waves by allowing a vibration film (membrane), which is on one side and can vibrate, to vibrate. Particularly in an acoustic medium, excellent wide-band characteristics can be easily achieved. In this specification, the acoustic waves are any of sound waves, ultrasound, and photoacoustic waves. For instance, the photoacoustic waves are caused by irradiating the inside of an object with light (electromagnetic waves), such as visible or infrared light.

In the above technological situations, Japanese Patent Application Laid-Open No. 2010-075681 proposes a probe receiving photoacoustic waves with a configuration where an optical reflection member for reflecting light with which an object has been irradiated is set larger than a receiving surface of the probe. Japanese Patent Application Laid-Open No. 2009-272824 proposes a capacitive ultrasonic probe including a protection layer on a vibration film. This probe has a configuration which includes the protection layer on an upper electrode and in which insulating organic material is arranged as protection layer material. In this specification, the vibration film of the membrane and the upper electrode are sometimes collectively called a vibration film.

SUMMARY OF THE INVENTION

When light for causing photoacoustic waves enters the capacitive photoacoustic probe, photoacoustic waves occur as noise on the receiving surface of the probe. Accordingly, an optical reflection layer is required to prevent light from being incident on the receiving surface. However, formation of the optical reflection layer may vary the spring constant and the amount of deformation of the vibration film of the electromechanical transducer in the probe; this variation should be avoided. Thus, the optical reflection layer is not directly formed on the vibration film. Instead, the optical reflection layer is formed on a support layer. The vibration film and the support layer with the optical reflection layer are caused to adhere to each other. In this case, the vibration film and the support layer with the optical reflection layer can suitably be caused to adhere to each other via an acoustic matching layer (a layer for conformity of acoustic impedance between the vibration film and the support layer).

However, in the case of using the probe that includes the vibration film and the support layer with the optical reflection layer stacked via the acoustic matching layer in the acoustic medium, stress is applied to the support layer and a solvent crack sometimes occurs. Occurrence of the solvent crack, in turn, causes a crack on the support layer with the optical reflection layer. Light enters through the crack to cause photoacoustic waves, thereby increasing noise. The solvent crack is also called Environmental Stress Cracking, which is known as a phenomenon of causing a crack affected by stress and environmental factors (chemical agents). Practically, not only the solvent, but also some chemical agents, such as oil and surfactants, exert analogous adverse effects.

Since the probe having the above configuration uses an adhesive for causing the vibration film to adhere to the support layer with the optical reflection layer, stress is unfortunately applied to the support layer. Because the optical reflection layer is required to allow photoacoustic waves to transmit, this layer is suitably a thin film. However, a pinhole is sometimes formed. Furthermore, the optical reflection layer is sometimes scratched. The scratch is caused by carelessness in fabrication of the probe, and by measuring an object while scanning the probe.

Through use of the probe including the optical reflection layer with a pinhole or a scratch in the acoustic medium, the acoustic medium may penetrate into the support layer to which stress is applied, thereby causing a solvent crack. Occurrence of the solvent crack widens the pinhole and scratch on the optical reflection layer, and increases the amount of transmission of light, which causes photoacoustic waves on the receiving surface of the probe. Accordingly, noise may increase.

To solve the problems, a probe of the present invention includes: an element including an element having at least one cell in which a vibration film containing one electrode out of two electrodes that are provided so as to interpose a space therebetween is vibratably supported; a support layer disposed on the vibration film; and an optical reflection layer disposed on the support layer. A protection layer against an acoustic medium is formed on the optical reflection layer.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

In the probe of the present invention, the support layer and the optical reflection layer on this support layer are provided on the vibration film of the cell, which is an acoustic wave receiving surface, and the protection layer against the acoustic medium is provided on the optical reflection layer. The probe is used with the acoustic medium intervening between the optical reflection layer and an object while being immobilized or moved with respect to the object. For instance, a cell includes: a second electrode formed, via a space, on a first electrode formed in contact with a substrate; a vibration film on which the second electrode is provided; and a vibration film supporter that supports the vibration film such that a space is formed between the first electrode and the vibration film. The cell can be fabricated according to a method of manufacturing any of types called a sacrificial layer type and a bonding type. An example of FIGS. 4A and 4B, which will be described later, includes a structure that can be fabricated according to the method of manufacturing a sacrificial layer type. An example of FIG. 5, which will be described later, includes a structure that can be fabricated according to the method of manufacturing the bonding type. The probe of the present invention, a light source and a data processing device can configure an object information acquisition apparatus. Here, the probe receives acoustic waves caused by irradiation of an object with light emitted from the light source, converts the waves into an electric signal. The data processing device generates an image data of the object using the electric signal.

Figure 4A:
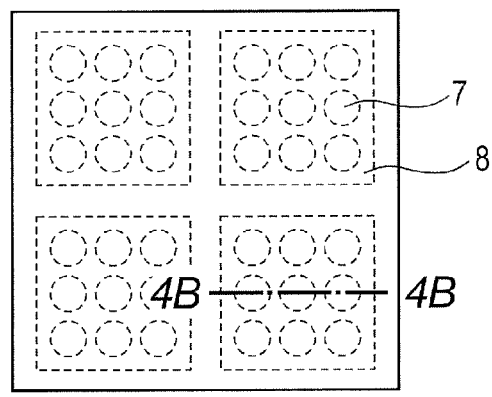
FIG. 4A is a top plan view of the probe using a capacitive electromechanical transducer.
Figure 4B:
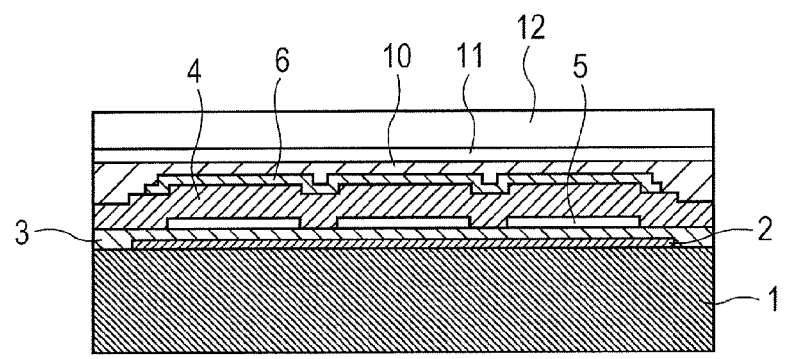
FIG. 4B is a sectional view of a probe using a capacitive electromechanical transducer (sacrificial layer type) taken along line 4B-4B.

Embodiments of the present invention will hereinafter be described. FIGS. 4A and 4B illustrate an example of a capacitive electromechanical transducer that includes an element including a plurality of cells. A probe of this embodiment includes at least the electromechanical transducer and a case (211, 311). FIG. 4A is a top plan view. FIG. 4B is a sectional view of FIG. 4A taken along line 4B-4B. The electromechanical transducer includes a plurality of elements 8 including cells 7. In FIGS. 4A and 4B, each of four elements 8 includes nine cells 7. However, the number of cells may be arbitrary.

Figure 5:
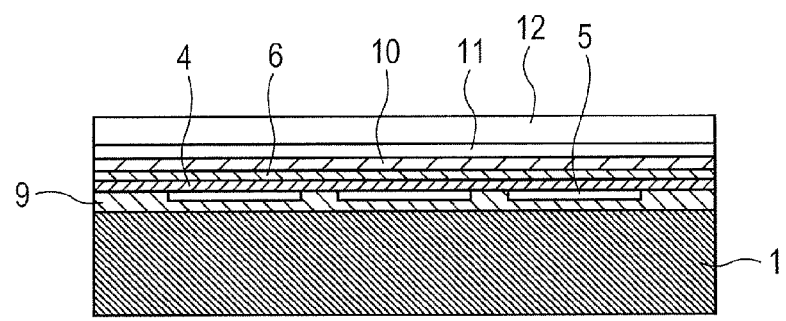
FIG. 5 is a sectional view of a probe using a capacitive electromechanical transducer (bonding type).

As illustrated in FIG. 4B, a cell 7 in this embodiment includes a substrate 1, a first electrode 2, an insulation film 3 on the first electrode 2, a space 5 such as cavity, a vibration film 4, and a second electrode 6 on the vibration film 4. In the cell, a vibration film including one of the two electrodes interposing the space is supported in a manner allowing the vibration film to vibrate. The substrate 1 is made of Si. Instead, this substrate may be an insulating substrate made of glass. The first electrode 2 is a metal film made of any of titanium and aluminum. In the case where the substrate 1 is made of silicon with a low resistance, the substrate itself can serve as the first electrode 2. The insulating film 3 can be formed by stacking a thin film made of silicon oxide. A vibration film supporter 9 supporting the vibration film 4 and the insulating film 3 is formed by stacking a thin film made of silicon nitride. The second electrode 6 can be formed of a metal film made of any of titanium and aluminum. FIGS. 4B and 5 illustrate an acoustic matching layer 10, an optical reflection member 11, and a protection layer 12. These components will be described later.

The electromechanical transducer of this embodiment can be formed using the method of manufacturing a bonding type. A cell 7 having the bonding type configuration illustrated in FIG. 5 is adapted to provide a space 5 such as cavity, a vibration film 4, a vibration film supporter 9, and a second electrode 6 on a silicon substrate 1. Here, the silicon substrate 1 having a low resistance also serves as the first electrode. Instead, the substrate may be an insulating glass substrate. In this case, a metal film (one of titanium and aluminum) to serve as the first electrode 2 is formed on the substrate 1. The vibration film 4 is formed of a junction silicon substrate. Here, the vibration film supporter 9 is made of silicon oxide. Instead, this supporter may be formed by stacking a thin film made of silicon nitride. The second electrode 6 is formed of a metal film made of aluminum.

A principle of driving the probe of this embodiment will be described. The cell is formed of the first electrode 2 and the vibration film that interpose the space 5. Accordingly, to receive acoustic waves, a direct current voltage is applied to one of the first electrode 2 and the second electrode 6. When the acoustic waves are received, the acoustic waves deform the vibration film to change the distance (height) of the space. Accordingly, the capacitance between the electrodes is changed. The change in capacitance is detected from one of the first electrode 2 and the second electrode 6, thereby allowing the acoustic waves to be detected. The element can also transmit acoustic waves by applying an alternating voltage to one of the first electrode 2 and the second electrode 6 to vibrate the vibration film.

Figure 1:
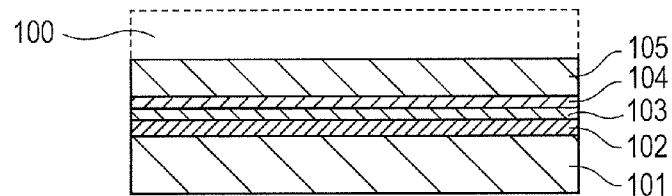
FIG. 1 is a sectional view for describing a photoacoustic probe of the present invention.

Next, a layer configuration on the vibration film of the photoacoustic probe according to this embodiment will be described with reference to FIG. 1. The probe has a configuration including an acoustic matching layer 102, a support layer 103, an optical reflection layer 104 and a protection layer 105, which are stacked on a photoacoustic probe substrate 101 including a receiving part. The support layer 103 and the optical reflection layer 104 configure the optical reflection member. The protection layer 105 is in contact with an acoustic medium 100 propagating photoacoustic waves. The acoustic medium 100 may be any of materials capable of transmitting photoacoustic waves; the medium may be castor oil, DIDS (sebacic acid diisodecyl ester), polyethylene glycol, ethanol, isotonic sodium chloride solution, and water. As described above, the probe substrate 101 includes: the receiving part provided with a membrane (vibration film) made of one of single crystal silicon and silicon nitride on the cavity formed on the single crystal silicon substrate; and electrodes.

The acoustic matching layer 102 is formed on the membrane of the receiving part. The acoustic matching layer 102 can suitably be made of what has a low Young's modulus that does not largely change mechanical characteristics, such as the spring constant of the membrane. More specifically, a suitable Young's modulus is 0 MPa or more and 100 MPa or less. The Young's modulus of 100 MPa or less alleviates adverse effects on the vibration film due to the stress of optical reflection layer 104. Since the stiffness (Young's modulus) is sufficiently low, the substantial mechanical property of the vibration film 7 is not changed. Furthermore, the acoustic matching layer 102 is suitably made of material having an acoustic impedance equivalent to that of the membrane. More specifically, the suitable acoustic impedance ranges from 1 MRayls to 2 MRayls. The acoustic matching layer 102 can be made of material, for instance, silicone rubber of bridged polydimethylsiloxane (PDMS). PDMS has a small Young's modulus of about 1 MPa, and an acoustic impedance of 1 to 2 MRayls (1 MRayls=1×10$^6$ kg·m$^{-2}$·s$^{-1}$. Hereinafter, MRayls will be used), which is equivalent to the acoustic impedance of the membrane. Accordingly, reflection of acoustic waves at the interface between the vibration film and the acoustic matching layer 102 can be suppressed. The acoustic impedance can be adjusted by adding silica particles to PDMS. Thus, the acoustic impedance is adjusted according to material used, thereby allowing photoacoustic waves to be efficiently received.

The optical reflection layer 104 is a film for reflecting light for causing the object to emit photoacoustic waves, and can be made of material having a high reflectance in a wavelength region of light to be used (e.g., about 700 to 1000 nm). The suitable reflectance is at least 80% in the wavelength region of light to be used. More suitable reflectance is 90% or higher. For instance, a metal film made of one of Au, Ag, Al and alloys therewith can be employed. The suitable thickness of the optical reflection layer 104 is equal to or less than 10 µm. In the case of using Au, Au has a high acoustic impedance of about 63 MRayls. To prevent ultrasound from being reflected owing to mismatching of the acoustic impedance, the thickness is required to be sufficiently small. To form an Au thin film, one of methods of forming a thin film, such as vapor deposition and sputtering, can be employed. However, the method is not limited thereto. Instead, a conventionally known method can be employed. In the case of using one of vapor deposition and sputtering, the thickness of Au film can range from 0.05 to 0.2 µm. A dielectric multilayer film may be formed on a metal film to further increase the reflectance. A dielectric multilayer film may be used as the optical reflection layer.

The optical reflection layer 104 can suitably be a film having a small thickness because this layer is required to transmit photoacoustic waves. However, in the case of forming the optical reflection layer employing any of vapor deposition and sputtering, a pinhole sometimes occurs owing to the manufacturing method. In the case of measuring an object while scanning the photoacoustic probe, the optical reflection layer tends to be scratched because the film thickness is small. The optical reflection layer 104 can be formed directly on the acoustic matching layer 102. However, this reflection layer can suitably be formed on the support layer 103. The acoustic matching layer 102 is made of material having a low Young's modulus. Accordingly, in the case of forming the optical reflection layer 104 directly on the acoustic matching layer, there is a possibility that the stress from the optical reflection layer deforms the acoustic matching layer. The acoustic matching layer 102 is made of material having a low Young's modulus. It is therefore difficult to reduce the surface roughness. Furthermore, it is difficult to increase the reflectance of the optical reflection layer on the acoustic matching layer. Thus, the optical reflection layer 104 can be suitably formed on the support layer 103 having a higher stiffness than the acoustic matching layer 102. The material of the support layer 103 may be a resin film whose principal ingredient is any of olefin resin, epoxy resin, acrylic resin, silicone resin, polyester resin, polycarbonate resin, polyurethane resin, and paraxylene resin. The support layer 103 suitably has an acoustic impedance close to that of the acoustic matching layer 102 to prevent ultrasound from reflecting owing to inconsistency of the acoustic impedance. More specifically, a suitable Young's modulus of the support layer 103 is 100 MPa or more and 20 GPa or less. The acoustic impedance can be about between 1 and 5 MRayls, inclusive. The acoustic impedance of the support layer 103 is configured close to the value of the acoustic impedance of the acoustic matching layer 102, thereby allowing the amount of reflection of acoustic waves to be reduced at the interface between the support layer 103 and the acoustic matching layer 102.

For instance, in the case of using PDMS as the acoustic matching layer 102, the support layer 103 can suitably be made of any of olefin resins, among which polymethylpentene resin can more suitably be used. In this case, PDMS may function as an adhesive layer for the ultrasonic probe substrate 101 and the support layer 103. However, this usage does not limit the scope. Instead, these components can adhere to each other using adhesive. However, in the case of causing the ultrasonic probe substrate 101 and the support layer 103 to adhere to each other via the acoustic matching layer 102 and the adhesive, stress may be applied to the support layer 103. Formation of the protection layer 105 on the optical reflection layer 104 prevents the acoustic medium from penetrating into the support layer, even if any of a pinhole and a scratch is formed when the optical reflection layer is formed. Formation of the protection layer 105 can prevent the optical reflection layer from being scratched when the photoacoustic probe is scanned. That is, the protection layer 105 of the present invention is formed on the optical reflection layer 104, and resistant to penetration (transmission) of the acoustic medium 100. The protection layer 105 suitably has a lower transmittance of the acoustic medium 100 than the optical reflection layer 104. More specifically, the suitable transmittance of the acoustic medium is equal to or less than $10^{-3}$ g/(m$^2$ day). The more suitable rate is $10^{-5}$ g/(m$^2$ day) or less. Thus, the number of scratches does not increase, and, if any of a pinhole and a scratch is formed on the optical reflection layer, the crack does not widen. Accordingly, noise can be prevented from increasing.

In the case where the degree of swelling (the degree of property absorbing water from a dry state to swell) of the protection layer 105 with respect to the acoustic medium 100 is high, the acoustic medium tends to penetrate into the support layer 103 and cause a crack in a state where stress remains in the support layer. As a favorable condition that does not cause a solvent crack, the degree of swelling of the protection layer 105 with respect to acoustic medium 100 can suitably be equivalent to or less than the degree of swelling of the support layer 103 with respect to the acoustic medium 100. That is, the suitable degree of swelling of the protection layer 105 with respect to the acoustic medium 100 is equal to or less than the degree of swelling of the support layer 103. More specifically, the rate of change in mass of the protection layer 105 in the case where the protection layer 105 is soaked in the acoustic medium is equal to or less than 1%. Furthermore, the protection layer 105 can suitably be formed such that the inner stress of the protection layer 105 or stress applied to the protection layer 105 is lower than the stress applied to the support layer 103. Reduction of stress applied to the protection layer 105 can, in turn, reduce the rate of occurrence of a solvent crack. The stress applied to the protection layer 105 can suitably be less than a threshold stress of crack at which a crack is caused owing to the acoustic medium. The film thickness of the protection layer 105 can suitably be equal to or less than 10 µm.

The protection layer 105 allows the photoacoustic waves to transmit, and the light transmittance can be at least 85% in the wavelength region of light to be used (e.g., 700 to 800 nm). For instance, the protection layer 105 can be formed of one of materials, such as olefin resin, epoxy resin, acrylic resin, silicone resin, polyester resin, polycarbonate resin, polyurethane resin and paraxylene resin. Methods of forming the resin may be the dip coating, spin coating, sol-gel method, spraying method, and chemical vapor deposition. However, the method is not limited thereto, a publicly known manufacturing method can be employed. Paraxylene can be formed by a suitable method of forming the protection layer 105 at a low stress according to the chemical vapor deposition method. Use of the chemical vapor deposition method can form the paraxylene resin on the optical reflection layer 104 as a conformal and pinhole-free thin film with low stress. Through use of the chemical vapor deposition method, paraxylene resin can be formed to have a film thickness of a several micrometers. Accordingly, attenuation of photoacoustic waves is low. The film is made of paraxylene resin, which is a high molecule film with a molecular weight of about 500 thousand. Accordingly, the degree of swelling with respect to the acoustic medium is small.

Thus, in the photoacoustic probe of this embodiment, formation of the protection layer on the optical reflection layer can prevent the acoustic medium from penetrating into the support layer even with a pinhole or a scratch caused when the optical reflection layer is formed. Furthermore, formation of the protection layer can prevent the optical reflection layer from being scratched during use of the probe while being scanned. Accordingly, penetration of the acoustic medium into the support layer through a pinhole or a scratch of the optical reflection layer can be suppressed, and occurrence of a solvent crack can, in turn, be suppressed. The protection layer that has a lower stress than the support layer and a lower degree of swelling than the degree of swelling of the acoustic medium into the support layer can suitably be formed on the optical reflection layer. This configuration can suppress occurrence of a solvent crack. As a result, the number of scratches on the optical reflection layer does not increase, and, even if a pinhole or a scratch is on the optical reflection layer, the crack does not widen. Accordingly, noise can be prevented from increasing.

Examples will hereinafter be described.

Example 1

Figure 2:
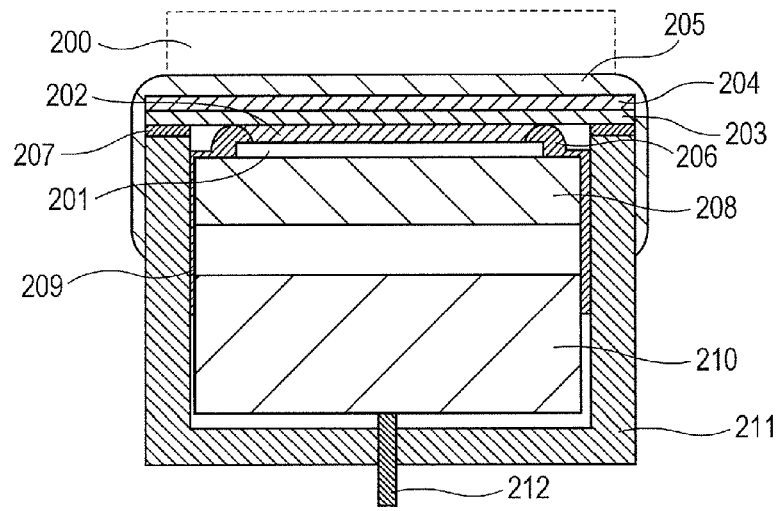
FIG. 2 is a sectional view of a photoacoustic probe according to Example 1 of the present invention.

Referring to FIG. 2, the probe of Example 1 of the present invention will be described. In this example, the protection layer is formed of paraxylene resin (parylene). A probe substrate 201 includes: a receiving part including a membrane made of any of single crystal silicon and silicon nitride on a cavity formed on the single crystal silicon substrate; and electrodes. The probe substrate 201 is fixed to the device board 208, and electrically connected to a pad (not illustrated) on the device board 208 by wire bonding. Wires and the pad are protected by seal members 206. The receiving part, which receives photoacoustic waves, has dimensions of 30 mm×20 mm, and is formed between two seal members 206. A signal of receiving photoacoustic waves from the receiving part of the probe substrate 201 is connected to a circuit 210 through a flexible substrate 209. The signal having passed through the circuit 210 is connected to the signal processor (not illustrated) through a cable 212.

An acoustic matching layer 202 on the probe substrate 201 is formed of polydimethylsiloxane (PDMS). PDMS has a small Young's modulus of about 1 MPa, and an acoustic impedance of 1 to 2 MRayls, which is equivalent to that of the acoustic impedance of the membrane of the receiving part. PDMS also functions as material of causing the support layer 203 on which an optical reflection layer 204 is formed to adhere to the probe substrate 201. If the film thickness of PDMS is too small, the force of adhesion is reduced. Accordingly, the thickness is 50 to 500 µm. The support layer 203 is made of polymethylpentene resin among olefin resins, and has a film thickness of 100 µm. The polymethylpentene resin has a higher stiffness than PDMS. Accordingly, the stress of the optical reflection layer 204 does not deform the support layer 203. The optical reflection layer 204 has a three-layer configuration of Au/Cr/SiO$_2$ (thickness=150 nm/10 nm/100 nm). SiO$_2$ is used for increasing the barrier property against a solvent. Cr is used for increasing a close contact property between the Au and SiO$_2$. A part of the support layer 203 on and above the receiving surface of the probe substrate 201 adheres to a case 211 via an adhesive layer 207. This configuration prevents an acoustic medium 200 from penetrating into the case 211.

A protection layer 205 made of parylene is formed on the optical reflection layer 204 using a chemical vapor deposition method. The protection layer 205 has a film thickness of 3 µm. The paraxylene resin can be formed into a low stress film that is conformal and pinhole-free, on the optical reflection layer 204, using the chemical vapor deposition. In the case where the support layer 203 made of polymethylpentene resin on which the optical reflection layer 204 is formed adheres to the probe substrate 201 using PDMS, calculation according to the finite element method shows that a stress of 60 MPa is applied to the support layer 203. Meanwhile, in the case of forming paraxylene resin using the chemical vapor deposition method, the stress is several megapascal, which hardly causes a solvent crack by the acoustic medium 200. Paraxylene resin is thus formed into a film of high molecule having a molecular weight of about 500 thousand. Accordingly, the degree of swelling of the protection layer with respect to the acoustic medium is lower than the degree of swelling of the support layer 203.

Thus, in the photoacoustic probe of Example 1, formation of the protection layer 205 made of paraxylene resin prevents the acoustic medium from penetrating into the support layer 203 through a pinhole or a scratch on the optical reflection layer 204. Accordingly, no solvent crack is caused. Even with a pinhole or a scratch on the optical reflection layer 204, the crack is therefore prevented from widening, thereby allowing noise to be reduced. In the case of measuring the object while scanning the photoacoustic probe, formation of the protection layer 205 prevents the optical reflection layer from being newly scratched. Accordingly, a solvent crack is prevented from occurring, and a photoacoustic probe with low noise can be fabricated. In Example 1, one protection layer 205 is formed. The number of the layers is not limited thereto. A plurality of layers may be formed. For instance, a layer suitable for preventing a scratch from occurring and a layer suitable for preventing a solvent crack from occurring may be separated from each other. Thus, a plurality of protection layers for the respective functions can be adopted.

Example 2

Figure 3:
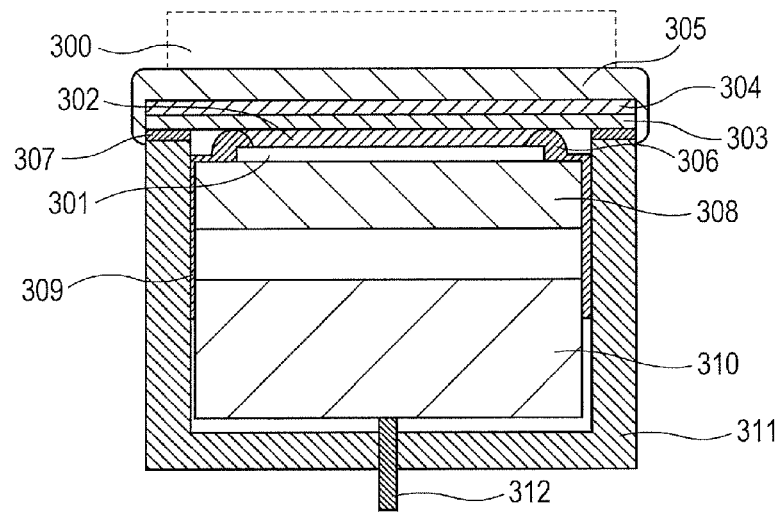
FIG. 3 is a sectional view of a photoacoustic probe according to Example 2 of the present invention.

Referring to FIG. 3, a photoacoustic probe of Example 2 according to the present invention will be described. In Example 2, the protection layer is formed using the spraying method. Example 2 has a configuration substantially equivalent to that of Example 1. In FIG. 3, components assigned with 300s having the last two digits identical to those of 200s illustrated in FIG. 2 indicate components having functions analogous to those illustrated in FIG. 2. In this example, the spraying method is employed as a method of forming a protection layer 305. The spraying method can form polyurethane into a film having a thickness of 10 µm or less. Such a method can also exert advantageous effects equivalent to those of Example 1.

Example 3

Figure 6:
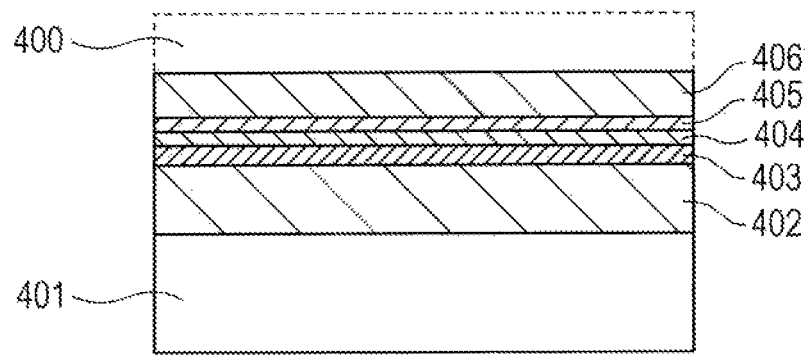
FIG. 6 is a sectional view of a photoacoustic probe according to Example 2 of the present invention.

Referring to FIG. 6, a photoacoustic probe of Example 3 according to the present invention will be described. The probe of this example has a layer configuration on a vibration film as illustrated in FIG. 6. The probe has a configuration where a stress alleviation layer 402 having functions of stress alleviation and for acoustic conformity, a support layer 403, a gas barrier layer 404, an optical reflection layer 405 and a protection layer 406 are stacked on a photoacoustic probe substrate 401 including a receiving part. The stress alleviation layer 402 is formed of PDMS and has, for instance, an acoustic impedance of about 1.5 MRayls. The support layer 403 is made of polymethylpentene (TPX) and has, for instance, an acoustic impedance of about 1.8 MRayls. The gas barrier layer 404 is made of $SiO_2$ and has a gas barrier property and moisture resistance. The optical reflection layer 405 is formed of Au/Cr. The gas barrier layer 404 and the optical reflection layer 405 are thin. Accordingly the acoustic impedances thereof have substantially no effects on acoustic conformity. The protection layer 406 in contact with the acoustic medium 400 is formed of parylene, which is a polymer of paraxylene series and has, for instance, an acoustic impedance of about 2.8 MRayls. The support layer, the gas barrier layer and the optical reflection layer configure the optical reflection member. Such a configuration can also exert advantageous effects equivalent to those of Example 1.

Example 4

The probe including the electromechanical transducer described in the embodiments and the examples is applicable to an object information acquisition apparatus using acoustic waves. Acoustic waves from an object are received by the electromechanical transducer. Through use of an output electric signal, object information in which an optical property value of the object, such as the optical absorption coefficient, is reflected can be acquired.

Figure 7:
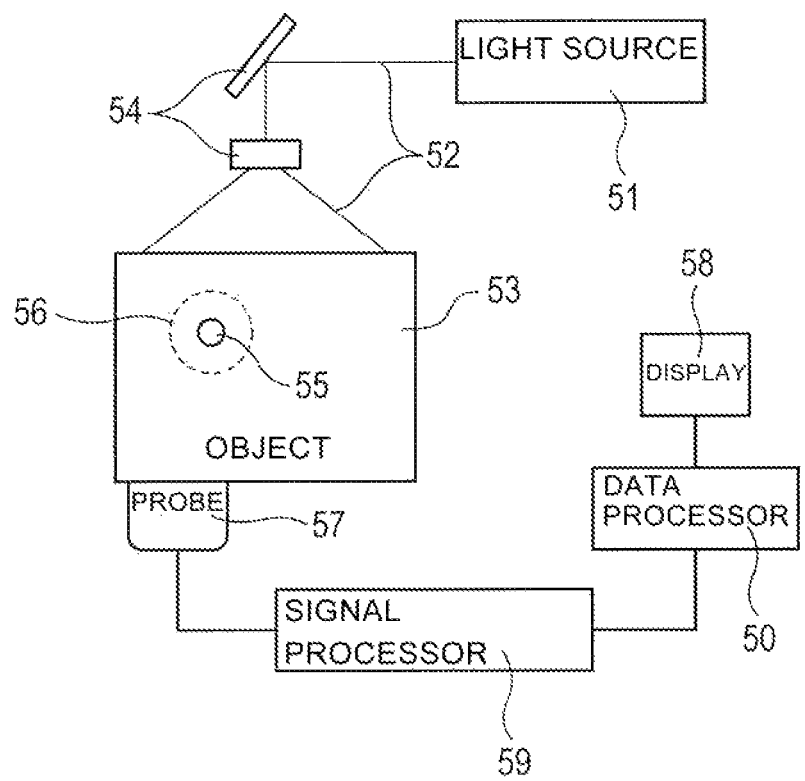
FIG. 7 is a diagram illustrating an object information acquisition apparatus using the probe of the present invention.

FIG. 7 illustrates an object information acquisition apparatus using photoacoustic effects according to this example. An object 53 is irradiated with pulsed light 52 emitted from a light source 51 via optical elements 54, such as a lens, a mirror and an optical fiber. A light absorber 55 in the object 53 absorbs the energy of the pulsed light and generates photoacoustic waves 56, which are acoustic waves. A probe 57 including a casing for accommodating an electromechanical transducer receives the photoacoustic waves 56, converts the waves into an electric signal and outputs the signal to a signal processor 59. The signal processor 59 performs a signal process, such as A/D conversion and amplification, on the input signal, and outputs the signal to a data processor 50. The data processor 50 acquires object information (object information in which an optical property value of the object, such as an optical absorption coefficient is reflected) as an image data, using the input signal. The display 58 displays an image based on the image data input from the data processor 50. The probe may be any of a type of being mechanically scanned and a type (hand-held type) of being moved by a user, such as any of a doctor and a technician, with respect to an object.

The probe of the present invention includes the protection layer against the acoustic medium, on the optical reflection layer. Accordingly, penetration of the acoustic medium into the support layer through a pinhole or a scratch on the optical reflection layer is suppressed, and occurrence of a solvent crack can be suppressed. Even with a pinhole or a scratch on the optical reflection layer, the scratch on the optical reflection layer can thus be prevented from being widening. Accordingly, noise due to occurrence of photoacoustic waves on the receiving surface of the probe can be prevented from increasing. Even in the case of measuring the object while scanning the probe, formation of the protection layer suppresses occurrence of a new scratch on the optical reflection layer. Accordingly, occurrence of a solvent crack on the support layer can be suppressed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-083415, filed Mar. 31, 2012, which is hereby incorporated by reference herein in its entirety.

What is claimed is:

1. A probe comprising:
   an element having at least one cell in which a vibration film containing one electrode out of two electrodes that are provided so as to interpose a space therebetween is vibratably supported;
   a support layer comprising a resin disposed over the vibration film;
   an optical reflection layer disposed on the support layer;
   a protection layer formed on the optical reflection layer to oppose an acoustic medium; and
   an acoustic matching layer formed on the vibration film, the support layer being disposed on the acoustic matching layer,
   wherein the support layer supports the optical reflection layer,
   wherein the acoustic matching layer is provided for conformity of acoustic impedance between the vibration film and the support layer, and
   wherein the protection layer has a thickness equal to or less than 10 μm and a principal ingredient comprising a resin.

2. The probe according to claim 1, wherein the protection layer has a lower transmittance of the acoustic medium than the optical reflection layer.

3. The probe according to claim 1, wherein the protection layer has a degree of swelling with respect to the acoustic medium lower than a degree of swelling of the support layer.

4. The probe according to claim 1, wherein the optical reflection layer is a metal film made of one of Au, Ag, Al and material including the same, and has a film thickness between 0.05 to 0.2 μm, inclusive.

5. The probe according to claim 1, wherein a principal ingredient of the support layer is any of olefin resin, epoxy resin, acrylic resin, silicone resin, polyester resin, polycarbonate resin, polyurethane resin, and paraxylene resin.

6. The probe according to claim 1, wherein the acoustic medium is any of castor oil, DIDS (sebacic acid diisodecyl ester), polyethylene glycol, ethanol, isotonic sodium chloride solution, and water.

7. The probe according to claim 1, wherein the protection layer has a degree of swelling with respect to the acoustic medium that is equivalent to or lower than the degree of the support layer, and stress of the protection layer is smaller than stress of the support layer.

8. The probe according to claim 1, wherein the protection layer allows an acoustic wave to pass, and a light transmittance in a wavelength region of light to be used is at least 85%.

9. The probe according to claim 1, wherein a principal ingredient of the protection layer is any of olefin resin, epoxy resin, acrylic resin, silicone resin, polyester resin, polycarbonate resin, polyurethane resin, and paraxylene resin.

10. The probe according to claim 1, wherein the protection layer is formed by a chemical vapor deposition method.

11. An object information acquisition apparatus comprising:
- the probe according to claim 1;
- a light source; and
- a data processing device,
- wherein the probe receives an acoustic wave caused by irradiation on the object with light emitted from the light source and converts the wave into an electric signal, and
- wherein the data processing device acquires information on the object using the electric signal.

12. A probe comprising:
- a capacitive electromechanical transducer including a first electrode, a vibration film, and a second electrode, a space being provided between the first and second electrodes so that the vibration film can vibrate with the second electrode due to receiving an acoustic wave;
- a support layer comprising a resin disposed over the vibration film;
- an optical reflection layer transmitting the acoustic wave and disposed on the support layer;
- a protection layer disposed on the optical reflection layer; and
- an acoustic matching layer formed on the vibration film, the support layer being disposed on the acoustic matching layer,
- wherein the support layer supports the optical reflection layer,
- wherein the acoustic matching layer is provided for conformity of acoustic impedance between the vibration film and the support layer, and
- wherein the protection layer has a thickness equal to or less than 10 μm and a principal ingredient comprising a resin.

13. A probe for receiving photoacoustic waves caused by irradiation of an object with light, said probe comprising:
- a transducer including a first electrode, a vibration film, and a second electrode, a space being provided between the first and the second electrodes so that the vibration film can vibrate with the second electrode;
- a support layer disposed over the vibration film;
- an acoustic matching layer disposed between the support layer and the vibration film;
- an optical reflection layer, for reflecting the light, disposed on the support layer; and
- a protection layer disposed on the optical reflection layer.

14. The probe according to claim 13, wherein the support layer has a Young's modulus that is 100MPa or more and 20GPa or less.

15. The probe according to claim 13, wherein the support layer has an acoustic impedance that is between 1 and 5 MRayls.

16. The probe according to claim 13, wherein the support layer comprises a resin.

17. The probe according to claim 13, wherein the protection layer allows an acoustic wave to pass, and a light transmittance in a wavelength region of light to be used is at least 85%.

18. The probe according to claim 14, wherein the probe is used with an acoustic medium intervening between the protection layer and an object.

19. The probe according to claim 18, wherein the protection layer has a transmittance for the acoustic medium equal to or less than $10^{-3}$ g/(m$^2$·day).

20. The probe according to claim 13, wherein a thickness of the protection layer is equal to or less than 10μm.

21. The probe according to claim 13, wherein the protection layer includes a resin.

22. The probe according to claim 13, wherein the optical reflection layer includes a metal film.

23. The probe according to claim 13, wherein a thickness of the optical reflection layer is equal to or less than 10μm.

24. An object information acquisition apparatus comprising:
- the probe according to claim 13;
- a light source; and
- a data processing device,
- wherein the probe receives an acoustic wave caused by irradiation on the object with light emitted from the light source and converts the wave into an electric signal, and
- wherein the data processing device acquires information on the object using the electrical signal.

25. The probe according to claim 13, wherein the optical reflection layer is a film for reflecting light for causing an object to emit photoacoustic waves and for transmitting photoacoustic wave generated in the object.

26. The probe according to claim 13, wherein the transducer is a capacitive type transducer.

27. A probe for receiving photoacoustic waves caused by irradiation of an object with light, said probe comprising:
- a transducer including a first electrode and a second electrode;
- a support layer disposed over a vibration film;
- an optical reflection layer, for reflecting the light, disposed on the support layer;
- a protection layer disposed on the optical reflection layer; and
- an acoustic matching laying between the vibration film and the support layer.

28. The probe according to claim 27, wherein the protection layer allows an acoustic wave to pass, and a light transmittance in a wavelength region of light to be used is at least 85%.

29. The probe according to claim 27, wherein the protection layer has a transmittance for the acoustic medium equal to or less than $10^{-3}$ g/(m$^2$·day).

30. The probe according to claim 27, wherein the thickness of the protection layer is equal to or less than 10μm.

31. The probe according to claim 27, wherein the protection layer includes a resin.

* * * * *